United States Patent [19]

Frindel et al.

[11] Patent Number: 5,114,926
[45] Date of Patent: May 19, 1992

[54] TETRAPEPTIDE INHIBITING THE ENTRY INTO CYCLE OF HEMOPOIETIC STEM CELLS PROCESSES FOR ITS PREPARATION, AND ITS USES

[75] Inventors: Emilia Frindel, Paris; Maryse Lenfant, Gif Sur Yvette; Martine Guigon, Neuilly; Johanna Bakala, Paris, all of France

[73] Assignees: Institut National De La Sante Et De La Recherche Medicale; Institut Gustave Roussy, both of Paris, France

[21] Appl. No.: 313,972

[22] PCT Filed: Jul. 16, 1987

[86] PCT No.: PCT/FR87/00281

§ 371 Date: Mar. 17, 1989

§ 102(e) Date: Mar. 17, 1989

[87] PCT Pub. No.: WO88/00594

PCT Pub. Date: Jan. 28, 1988

[30] Foreign Application Priority Data

Jul. 18, 1986 [FR] France .................. 86 10486

[51] Int. Cl.⁵ .................. C07K 5/10; A16K 37/02
[52] U.S. Cl. .................. 514/18; 514/19; 530/330
[58] Field of Search .................. 514/18, 19; 530/330

Primary Examiner—Lester L. Lee
Assistant Examiner—E. J. Kraus
Attorney, Agent, or Firm—Larson and Taylor

[57] ABSTRACT

The invention relates to a tetrapeptide corresponding to the general formula

Ser-Asp-Lys-Pro—OH and its substitution derivatives by one or several groups, identical or different, currently used in the chemistry of peptides for biological use, as well as their pharmaceutically acceptable salts, in particular the tetrapeptide Ser-(N-Ac)-Asp-Lys-Pro—OH which can be extracted, for example, from fetal calf marrow or obtained by peptide synthesis.

The peptide of the invention is particularly useful in the protection of bone marrow in the course of anti-cancer treatments by chemotherapy.

10 Claims, 1 Drawing Sheet

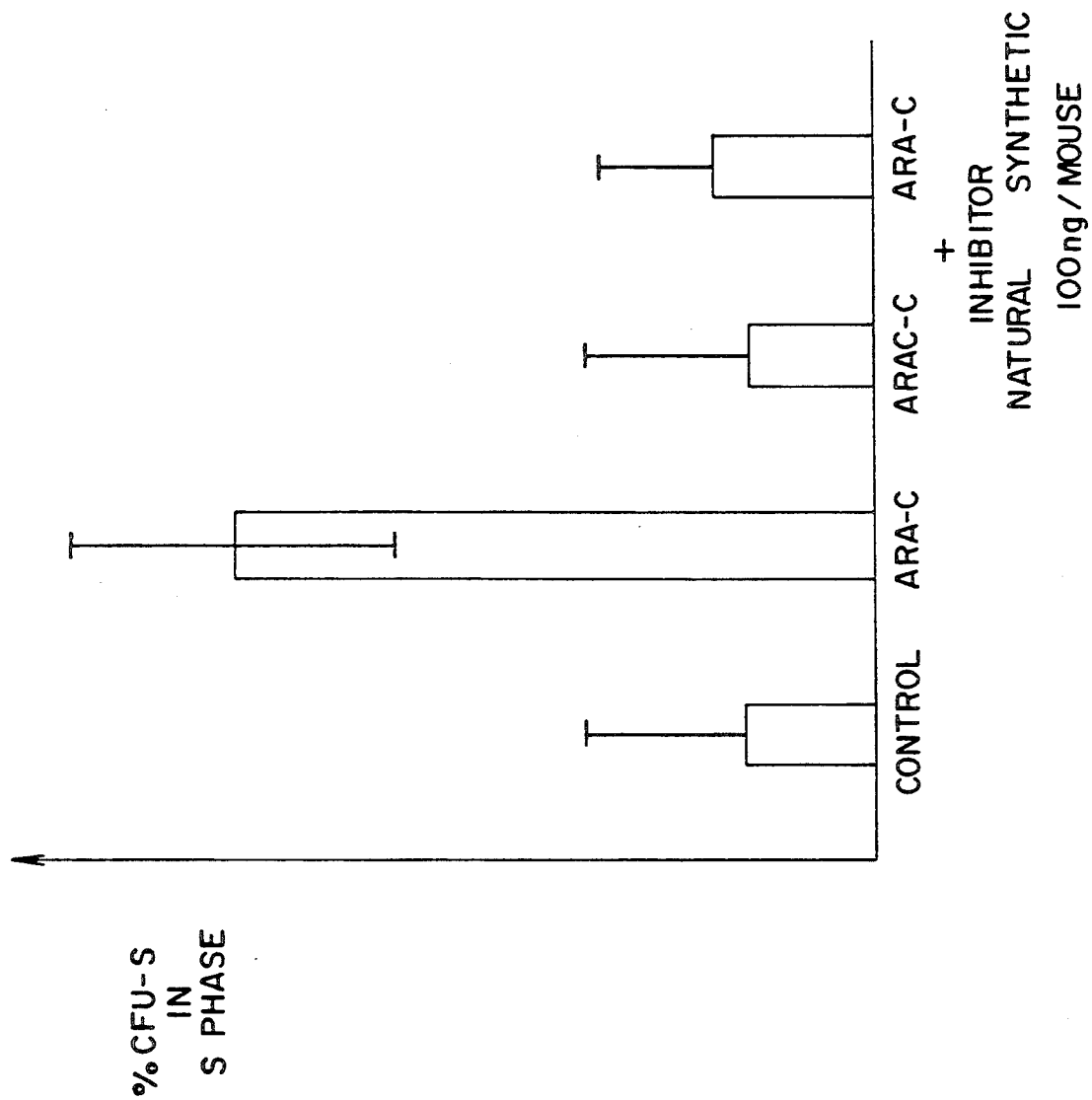

TETRAPEPTIDE INHIBITING THE ENTRY INTO CYCLE OF HEMOPOIETIC STEM CELLS PROCESSES FOR ITS PREPARATION, AND ITS USES

The invention relates to a novel tetrapeptide acting as an inhibitor of entry into cycle of hemopoietic stem cells as well as its usual derivatives in the field of peptides with biological activity.

The invention also relates to a process for the extraction of this tetrapeptide from biological substances, particularly from fetal calf marrow and a process for its synthesis, as well as of its substitution derivatives, by the chemical route.

It also relates to the uses of this peptide and of its substitution derivatives in biology and in medicine, particularly in the protection of bone marrow in the course of anti-cancer treatments by chemotherapy.

The use of medicines in the treatment of cancers is limited by their toxic effects on healthy tissues, and in particular, on the hemopoietic tissue. The repeated use of these drugs results in a large number of cases either in lethal marrow aplasia, or a secondary leukaemia, or less serious hematological sequelae.

As the majority of anti-cancer medicines only act on proliferating cells, Applicants have thought that it would be possible to prevent hematological damages by protecting pluripotent stem cells by proliferation inhibitors.

Studies carried out by Applicants and previously published [see particularly E. Frindel and M. Guigon, Exp. Hemat., 5 (1977), 74-76, M. Guigon and E. Frindel, Bull. Cancer 68(2), (1981), 15-153, J. Wdzieczak-Bakala, M. Lenfant and M. Guigon, IRCS Med. Sci. 12 (1984) 868-869, J. Wdzieczak-Bakala, M. Guigon, M. Lenfant and E. Frindel, Biomed. Pharm. 37(1983), 467-471 and M. Guigon, J. Wdzieczak-Bakala, J. Y. Mary and M. Lenfant, Cell Tissue Kinet. 17(1984), 49-55] have shown that it was possible to reduce significantly, by administration of a specific inhibitor of stem cells, the lethality observed in animals in the course of treatments with cytosine arabinoside (Ara-C), a drug currently used for chemotherapy of cancer, whose use is limited by its injurious effect on bone marrow. That specific inhibitor which is extracted from certain biological substances, particularly from fetal calf bone marrow or fetal calf liver, protects the stem cells which are at the origin of all blood lines.

In fact, biological studies carried out show that the increase in survival observed can be attributed to a protection of the hemopoietic stem cells, CFU-S (Colony Forming Units in the Spleen) that is to say pluripotent stem cells capable of giving rise to clones in the spleen of mice irradiated at a lethal dose, this protection being due to the maintenance of said cells outside of the cellular cycle, by the inhibitor.

Published documents describe techniques enabling more or less purified extracts containing the specific inhibitor to be obtained, but in all cases the product finally obtained is not homogeneous and the yields are unsatisfactory. It has therefore not been possible up to now to isolate the active principle and to establish its structure.

Now, Applicants have now developed a novel extraction process which enables a homogeneous active fraction to be obtained from a biological material, particularly from fetal calf marrow.

This process comprises essentially the steps consisting of:
grinding the starting material with delipidation if necessary,
suspending the product obtained in a buffer at a pH close to 7, in the presence of a sulphur-containing reducing reagent, particularly dithioerythritol or preferably mercaptoethanol,
centrifuging the homogenizate at about 15,000 g for at least one hour,
subjecting the supernatant to ultrafiltration on a membrane having an exclusion limit close to 10,000 daltons,
subjecting the ultrafiltrate obtained to chromatography on a molecular sieve of the polyacrylamide gel type, with elution by a dilute solution of acetic acid,
subjecting the active fraction collected to fractionation on a reverse phase support of silica grafted with aliphatic residues, particularly with 18C, repeating this step preferably at least once; and
subjecting the novel active fraction collected to high pressure liquid chromatography on a reverse phase column of silica grafted with aliphatic residues, particularly with 18C, to obtain a homogeneous active fraction.

The "active fraction" is identified by biological tests, particularly as described in the experimental part which follows.

A detailed example, which is not limiting, of the practice of this extraction process is given in the experimental part of the present specification.

The combination of different analysis techniques, particularly NMR, mass spectrometry and analysis of the amino acid content by high pressure liquid chromatography (HPLC) has enabled the determination of the structure of the homogeneous product so isolated. This product is acetylated tetrapeptide of molecular weight 487, corresponding to the formula:

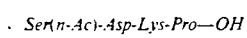

or

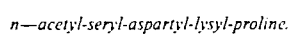

n—acetyl-seryl-aspartyl-lysyl-proline.

The results previously described did not permit one to think that the activity observed of the more or less purified extracts obtained could be due to a tetrapeptide of the above-identified type.

In fact, there had especially been observed a protective effect of mercaptoethanol on the inhibitory fraction which seemed due to the presence of thiol groups in the inhibitor molecule, the presence of such groups having been established in the relatively purified inhibitory fraction obtained previously (see IRCS Med. Sci. 12, (1984), 868-869).

In the same way, sugar residues having been detected, it was thought that the active principle could be of the glycopeptide type, this supposition being supported by the fact that the inhibitor concerned can be classified among the chalones or anthromones and that the majority of substances of this type are glycosylated.

The invention therefore relates to the tetrapeptide

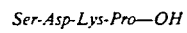

and its substitution derivatives by one or several groups protecting the peptides, identical or different, currently used in the chemistry of peptide for biological use. Advantageously, these groups are selected from among acetyl, benzyl, methyl, and phenyl. The derivative monoacetylated on the terminal nitrogen is most particularly preferred.

The invention also relates to the pharmaceutically acceptable salts of these compounds.

The tetrapeptide Ser-Asp-Lys-Pro—OH may be obtained by extraction from biological materials, particularly from fetal calf liver or marrow.

It can particularly be obtained by the process described generally above and in more detail in the experimental part. It is then in the acetylated (in the N-terminal position) form and may be used as such or be deacetylated according to conventional techniques in peptide chemistry.

The peptide according to the invention and its substitution derivatives can also be obtained by peptide synthesis, especially in the liquid phase.

The liquid phase peptide synthesis advantageously takes place by successive additions, from the terminal C end, of the appropriate amino acid groups, suitably substituted or protected on their reactive groups, with, when necessary, removal of the protective groups. p
The inhibitor obtained according to the invention does not seem to have species specificity (in the trials described here it is extracted from fetal calf marrow and is active in the mouse); it is therefore possible to contemplate using it, as well as its substitution derivatives, in the same way as their pharmaceutically acceptable salts, in numerous medical and biological applications in man and in the animal.

These compounds may be used for the protection of the bone marrow during anti-cancer treatments by chemotherapy.

In this case, they are advantageously formulated in a powder state and administered, in the presence of usual adjuvants and/or excipients, i.v. or s.c., in the course of the chemotherapeutic treatment. The frequency of the administrations and the amount of product administered depend essentially on the kinetics of the stem cells which can vary according to the therapeutic agent, its posology and the protocol of its use.

Other methods of "administration" may be envisaged, for example that consisting of causing the inhibitor to be produced in the organism of the patient by resorting to techniques of genetic engineering, for example by means of bacteria.

The tetrapeptide and its substitution derivatives according to the invention can besides be used for obtaining specific antibodies for the determination of the level of inhibitor circulating in the patients and the determination of its role in certain diseases of the hemopoietic system, as well as in the course of bone marrow graftings.

The use of these antibodies, in the case of hyperproduction of the inhibitor associated with pathologies, may also be envisaged.

I. EXTRACTION OF THE PEPTIDE N-ACETYL-SERYL-ASPARTYL-LYSYL-PROLINE

The raw material is constituted by fetal calf bone marrow preserved frozen. At each of the steps described below, the fractions isolated are supplemented with mercaptoethanol at the final concentration $10^{-2}M$.

5 kg of tissue are ground by means of a homogenizer of the Waring blender type (3 times, 60 sec.) in 40l of $10^{-2}M$ phosphate buffer, pH 7.2 in the presence of $10^{-2}M$ mercaptoethanol at 4° C. The suspension is centrifuged at 15,000 g for 1h 30.

The supernatant collected is ultrafiltered on membrane of the Sartorius 121 36 type which enables the separation of the molecules according to their molecular weight and the exclusion limit of which is $10^4$ daltons.

The ultrafiltrate is concentrated 20 times by evaporation under vacuum by means of "flash evaporator" (LUWA) type evaporator. The concentrate is then lyophilized. The yield is 16.5 g/kg and the fraction is active in the mouse at the dosage level of about 20 mg/mouse (activity determined according to one or the other of the protocols that are described below). The lyophilized powder (50 g) is then redissolved in 200 ml of a $10^{-2}M$ acetic acid solution (pH 3) then centrifuged (10 min., 15,000 g). The supernatant is chromatographed on a column of molecular sieve of the Biogel P-2 type, having about 0.07 to 0.04 mm "mesh opening" (200-400 mesh) (BIO-RAD), of dimensions $12.5 \times 100$ cm, and eluted with 20l of $10^{-2}M$ acetic acid (flow rate 400 ml/hour).

The active fraction is eluted with the elution ratio Ve/Vo 1.2-1.8. Ve being the elution volume and Vo the void volume of the column. The yield is 250 mg/kg of starting material and the fraction is active in the mouse at the dosage level of about 5 µg/mouse.

The active fraction (10 mg) is then dissolved in 1 ml water, then fractionated successively onto two cartridges of reverse phase support of silica grafted with aliphatic residues with 18C of the Sep-pak C-18 type (WATERS). The cartridges are eluted in order with:

2 ml of $H_2O$
2 ml of a mixture $H_2O/CH_3OH$ (50/50)
2 ml of $CH_3OH$

The active fraction eluted with the mixture $H_2O/CH_2OH$ (50/50) is then concentrated in vacuum, at a temperature of about 20° C. on an apparatus of the Speed Vac type, then lyophilized.

The purification is continued by high pressure liquid chromatography on a reverse phase analytical column of octadecyl-silica of the ODS-Hypersil C-18 type, $(250 \times 4.6$ mm$)$ 5 µ (SFCC). The elution is done with the mixture $H_2O$, 0.1% $CF_3COOH$—MeOH (80-20) or the mixture $H_2O$, 0.1% $CF_3COOH$—$CH_3CN$ (95-5) with a flow rate of 1 ml/min. The detection of the fractions is carried out by measurement of the absorption at 215 nm.

The results obtained are as follows:

1. Solvent ($H_2O$, 0.1% $CF_3COOH$)/$CH_3OH$, (80/20) flow rate 1 ml/min.; retention time: 6 min.: one homogeneous peak.

2. Solvent ($H_2O$, 0.1% $CF_3COOH/CH_3CN$, (95/5) flow rate 1 ml/min.; retention time: 18 min: one homogeneous peak.

It is observed that this process enables the obtaining of a homogeneous product whose structure is determined as indicated below.

The overall yield is 60 µg/kg of starting material.
The fraction is active in the mouse at the dosage of about 100 ng/mouse.

II. DETERMINATION OF THE STRUCTURE OF THE ACTIVE PRINCIPLE

1. Analysis of the amino acids

After acid hydrolysis, the analysis by HPLC of the derivatives formed by reaction with orthophthaldialdehyde enables the presence of lysine, aspartic acid and serine to be observed. Analysis of the product by means of an amino acid analyzer, after acid hydrolysis and oxidation with sodium hypochlorite, enables the presence of proline to be observed and the presence of aspartic acid, serine and lysine to be confirmed.

2. NMR spectroscopy

The one dimension and two dimension NMR ($H_2O$ and $D_2O$) shows the presence of four amino acids (proline, lysine, aspartic acid, serine) and of an acetyl group. The $NH_2$ of the side chain of the lysine and the OH of the serine are free, the $NH_2$ of the amino acid parts of the serine, of the lysine and of the aspartic acid are substituted once. The probable structure is that of a peptide acetylated on the terminal $NH_2$.

3. Mass spectrometry

The mass spectrometry (MS) techniques in FAB (Fast Aatom Bombardment) have shown that this peptide has a molecular weight (M+1) of 488.

A study of the sequence of amino acids by a modification of mass spectrometry, namely the so-called MS-MS technique, has enabled it to be established that the complete primary structure of the peptide is:

$$Ser-N-Ac-Asp-Lys-Pro-OH$$

III. DESCRIPTION OF BIOLOGICAL TESTS

The biological activity of the fractions is measured by in vivo inhibition tests of the entry into cycle of the CFU-S, induced by an injection of Ara-C.

The CFU-S of the mouse, normally quiescent, enter into cycle after an injection of Ara-C. Applicants have shown that when the inhibitor is injected 6 hours after the drug, it prevents the entry of the CFU-S into DNA synthesis (S phase).

The number of CFU-S is determined by the technique of J. E. Till and E. A. McCulloch, Radiat. Res. 14, (1961), 213–222, whose principle rests on the capacity of CFU-S to form macroscopic colonies in the spleen. These colonies are clones descended from one CFU-S.

The proportion of CFU-S in S phase is determined by the method of A. J. Becker et al., Blood, 26, (1965), 296–308, based on the principle of cellular suicides. The incubation of the cells with a tritiated thymidine (precursor of DNA) solution leads to the selective death of the cells in phase of DNA synthesis by integration of a lethal dose of radioactivity (tritium) into the DNA molecule.

The tests are performed on SPF (Specific Pathogen Ffree)mice of Balb/C or CBA strain, aged from 2 to 3 months.

1. The control groups receive by the i.p. route the following treatment:

Time 0: Ara-C (10 mg—protocol I or 20 mg—protocol II) dissolved in 0.2 ml of saline;
Time 6H: 0.2 ml of saline;
Time 8H: sacrifice (protocol I);
Time 12H: sacrifice (protocol II).

2. The treated groups receive by the i.p. route:

Time 0: Ara-C (10 mg—protocol I or 20 mg—protocol II) dissolved in 0.2 ml of saline.
Time 6h: fraction to be tested dissolved in 0.2 ml of saline;
Time 8H: sacrifice (protocol I);
Time 12H: sacrifice (protocol II).

```
                Protocol I      Protocol II
                    ↓               ↓
    0           6   8              12
                                    hours
    |───────────|───|──────────────|
    ↑           ↑       ↖          ↗
   Ara-C    Inhibitor    ↘        ↙
                      Determination of
                      the number of CFU-S
                           in cycle.
```

For each of the groups, the bone marrow of the animals is collected and suspended in 2 ml of Medium 199 (EUROBIO). After the numbering and suitable dilution, 2 aliquots of $5 \times 10^6$ nucleated cells are incubated at 37° C. for 20 min. either with 1 ml of Medium 199 (Test A), or with 1 ml of tritiated thymidine (200 μCi) (Test B). A cellular suspension of 0.2 ml containing $8 \times 10^4$ to $1.2 \times 10^5$ nucleated cells is injected intravenously into the retro-orbital sinus of the irradiated receiver animals (9 Gy, 8 mice per experimental plot). Nine days later, the receiver mice are sacrificed, their spleen taken out and fixed in Bouin fluid (1% picric acid: 720 g; formol: 240 g; acetic acid: 4 g, per 1 l of fluid). After some hours of fixation, the nodules visible macroscopically are counted.

If N and N' are the average numbers of the nodules obtained on the spleens of the receivers having received cells coming form tests A and B respectively, the proportion of CFU-S in phase of DNA synthesis is calculated by the formula:

$$\% \text{ of the } CFU\text{-}S \text{ in } S = \frac{N - N'}{N} \times 100$$

RESULTS

1. Inhibition of the entry into cycle of CFU-S

In the course of each purification step, a fraction active with respect to this test is isolated. However, a particularly interesting activity is observed with the homogeneous fraction obtained according to the invention, as is shown by the following table:

Inhibition of the entry into cycles of CFU-S by injection of 100 ng per mouse of the homogeneous fraction obtained according to the invention, according to protocol II.

TABLE I

| Treatment | % of CFU-S in DNA synthesis |
|---|---|
| Ara-C (20 mg) | 43 ± 9 |
| Ara-C (20 mg) + inhibitor (100 ng) | 7 ± 4 |

2. Activity on the survival of animals treated with lethal doses of Ara-C

The animals receive fractionated doses of Ara-C ($4 \times 925$ mg/kg) at times 0, 7, 24 and 30 hours. The tested fraction is administered at once 26 hours after the first injection of Ara-C. The survival of the animals is estimated 15–30 days after the treatment. In this protocol comprising lethal, repeated injections of Ara-C, it was shown that the concomitant administration of inhibitor enabled the definitive survival of a large number of animals. The results obtained are comparable with those observed when an isogeneic bone marrow grafting is performed in the treated animals, instead of using the inhibitor.

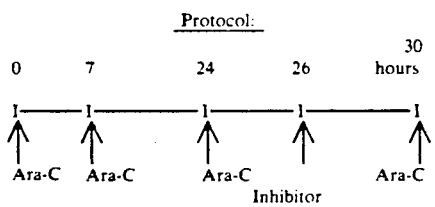

Protocol:

3. Absence of activity of the inhibitory fraction on the regression of EMT6 tumors The treatment of animal carries of the EMT6 tumor by 4 successive injections of Ara-C at times 0, 7, 24 and 30 hours followed by an injection of the inhibitor 26 hours after the first injection of Ara-C, does not prevent the therapeutic action of Ara-C with respect to tumor cells and permits the survival of the treated animals comparably with the results obtained following a bone marrow grafting.

4. Toxicity

The inhibitory fraction is devoided of toxicity with respect to CFU-S and does not result in any lethality in the treated mice, at the doses used.

IV. LIQUID PHASE SYNTHESIS OF NAC-SER-ASP-LYS-PRO-OH, WRITTEN CONVENTIONALLY ABREVIATED ACSDKP a) Synthesis of Boc-K(Z)-P—OH (I)

To a solution of Boc-K(Z)-OSu (4.01 mmoles) in DMF is added an aqueous solution of P (8.38 mmoles) in which 1.15 ml of triethylamine (8.38 mmoles) have been placed. The mixture is stirred overnight at room temperature.

After evaporation of the solvent, the residue is dissolved in ethyl acetate. The solution washed successively with a 5% citric acid solution, a 5% sodium carbonate solution and with water, is dried over $MgSO_4$. After evaporation of the solvent, the product thus obtained is characterized:

Yellowish oil: 3.98 mmoles; yield: 95%.

$[\alpha]_D = -38°$ (C = 1.0; MeOH).

Rf: 0.5 (MeOH/CHCl$_3$: 1/9); 0.24 (EtOAc/MeOH: 8/1).

The Rfs are determined by thin-layer chromatography on silica.

NMR performed in solution in CDCl$_3$: in agreement.

Note: it is recalled that

Boc = tert-butyloxycarbonyl;

Z = benzyloxycarbonyl;

Su = sulfonamide;

DMF = dimethylformamide.

b) Synthesis of Boc-D(OBzl)-K(Z)-P—OH (II)

To a solution of Boc-D(OBzl)-OSu (3.31 mmoles) in DMF is added a solution of TFA.K(Z)-P—OH (3.15 mmoles) in DMF containing 915 μl of triethylamine, namely 6.62 mmoles. The solution of TFA.K(Z)-P—OH is obtained by treatment of product (I) with a solution of TFA (10 equivalents) and anisol (1 equivalent) for 1 hour at 0° C. It is washed with hexane then with ether before being used for the following step. The mixture thus constituted is placed under stirring overnight at room temperature. After evaporation of the solvent, the residue is solubilized in ethyl acetate and washed as in a) before being characterized:

Oil: 2.17 mmoles; yield: 70%.

$[\alpha]_D = 20°$ (C = 1.2; MeOH).

Rf: 0.23 (MeOH/CHCl$_3$: 1/9).

NMR performed in solution in CDCl$_3$: in agreement.

Note: it is recalled that

TFA = trifluoroacetic acid; and

Bzl = benzyl.

c) Synthesis of Boc-S(Bzl)-D(OBZl)-K(Z)-P—OH (III)

According to the same sequence as in b), 1.47 mmoles of Boc-S-(Bzl)-Osu are added to 1.47 mmoles of TFA.D(OBzl)-K(Z)-P—OH.

The product obtained has the following characteristics:

Oil: 1.31 mmoles; yield: 89%.

$[\alpha]_D = -26°$ (C = 1.0; MeOH).

Rf: 0.29 (MeOH/CHCl$_3$: 1/9).

NMR carried out in solution in CDCl$_3$ supplemented with a small amount of MeOD to improve the solubility and the resolution of the spectra: in agreement.

d) Synthesis of AcS(Bzl)-D(OBzl)-K(Z)-P—OH (IV)

After elimination of the N-terminal Boc from product (III), the new blocking group is added in a single step. The final product, after washings, shows the following characteristics when 1 mmole of TFA.S(Bzl)D-(OBzl)k(Z)P—OH is used:

Oil: 0.77 mmole; yield: 77%.

$[\alpha]_D = -22.0$ (C = 1.0; MeOH).

Rf: 0.12 (CHCl$_3$/MeOH: 9/1); 0.54 (EtOAc/MeOH/CH$_3$COOH; 16/3/1).

NMR performed in solution in CDCl$_3$ supplemented with MeOD: in agreement.

e) Obtaining of Ac-S-D-K-P—OH (V)

Product (IV) in solution in methanol is subjected, after an addition of palladized carbon, to hydrogenolysis. After completion of the reaction, the methanol is evaporated and the residue is characterized.

This final product which is after lyophilization in the form of a white solid, is characterized by the same physico-chemical techniques as the natural peptide, namely:

analysis of amino acids;

high performance liquid chromatography;

NMR in solution in D$_2$O; and

FAB and FAB (MS-MS) mass spectrometry.

In all these techniques, a good correspondence observed of the results obtained for the synthetic product V with those obtained for the natural product.

In particular, the NMR spectra of the proton of the natural and synthetic peptides are wholly superposable as well as the mass spectra.

Analysis of this synthetic tetrapeptide by reverse phase HPLC on ODS-Hypersil C18 analytical column, under isocratic conditions, with the mixture CH$_3$CN/H$_2$O, 0.1% TFA [4.5/95.5], with a detection at 215 nm, enables the observation that the peak at 18 minutes, a 25° C. includes a slight shoulder which appears more distinctly in the first part of the peak at 24 minutes, at 15° C. This peak at 24 minutes, at 15° C. can be split into a peak of low intensity at 22 minutes, corresponding to the preceding shoulder, and into a peak at 24 minutes. The product corresponding to this peak possesses the biological properties of the natural peptide.

It is subjected to the previously described tests in relation with the natural inhibitor extracted according to the invention.

The percentages of CFU-S in phase of DNA synthesis obtained are collected in table II which follows.

TABLE II

| Dose of synthetic tetrapeptide/mouse | Control | ARA-C | ARA-C + synthetic tetrapeptide |
|---|---|---|---|
| 1. 100 ng | 20 | 44 | 12 |
| 2. 100 ng | 10 | 30 | 1 |
| 3. 100 ng | — | 55 | 17 |
| 4. 100 ng | 0 | 26 | 6 |
| 5. 50 ng | — | 35 | 13 |
| 6. 25 ng | 0 | 48 | 19 |
| 7. 100 ng | 0 | 36 | 10 |
| 8. 100 ng | 0 | 36 | 6 |
| mean | 5 | 38.7 | 10.5 |

Tests 1, 2 and 3 were carried out with the tetrapeptide obtained by a first synthesis, tests 4, 5, 6, 7 and 8 were performed with the tetrapeptide obtained by a second synthesis.

The results obtained are to be compared with those obtained with the natural product and which are shown in table I, on the one hand and in table III, on the other hand.

The latter results were obtained with the natural product extracted from two different batches a and B of bone marrow.

TABLE III

| Batch of bone marrow | dose/ mouse | Control | ARA-C | ARA-C + natural peptide |
|---|---|---|---|---|
| A (5 exp ) | 100 ng | 6.5 ± 13.9 | 40.7 ± 9.3 | 12.6 ± 14.8 |
| B (2 exp ) | 100 ng | 11.9 ± 16.3 | 47.4 ± 9 | 2.99 ± 13 |
| mean | | 9.2 | 44.1 | 7.8 |

Comparative study of tables I and III, on the one hand, and II, on the other hand, enables the observation that the synthetic peptide has a quite similar activity to that obtained with a natural peptide.

The results obtained are shown diagrammatically in the single appended drawing.

We claim:

1. Tetrapeptide, substantially pure and homogeneous, of the general formula:

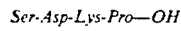

unsubstituted or having at least one of its amino, hydroxyl or carboxyl groups protected with protecting groups selected from the group consisting of acetyl, benzyl, methyl, phenyl, benzyloxycarbonyl and tert-butoxycarbonyl and pharmaceutically acceptable salts of said tetrapeptide.

2. Tetrapeptide according to claim 1, of the formula

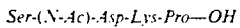

as well as its pharmaceutically acceptable salts.

3. Process for the extraction of the tetrapeptide according to claim 2, from biological materials, particularly from fetal calf liver or marrow, said process comprising essentially the steps of:

grinding the starting material with delipidation if necessary;

suspending the product obtained in a buffer at a pH close to 7, in the presence of a sulphur-containing reducing reagent;

centrifuging the homogenizate at about 15,000 l g for at least one hour;

subjecting the supernatant to ultrafiltration on a membrane having an exclusion limit close to 10,000 daltons;

subjecting the ultrafiltrate obtained to chromatography on a molecular sieve of the polyacrylamide gel type, with elution by a dilute solution of acetic acid;

subjecting the active fraction collected to fractionation on a reverse phase support of silica bonded with aliphatic residues; and subjecting the novel active fraction collected to high pressure liquid chromatography on a reverse phase column of silica bonded with aliphatic residues to obtain a homogeneous active fraction.

4. Process according to claim 3, wherein the sulphur containing reducing agent is dithioerythritol or mercaptoethanol.

5. Process according to claim 3, wherein the fractionation step is repeated at least once.

6. Process according to claim 3, wherein the reverse phase support of silica is bonded with aliphatic residues with 18C.

7. Process according to claim 3, wherein the reverse phase column of silica is bonded with aliphatic residues with 18C.

8. Process for synthesis of the tetrapeptide according to claim 6, said process consisting essentially of adding successively in liquid phase, from the C terminal end, the suitable amino acid groups, suitably substituted or protected on their reactive groups, and when necessary, eliminating the protecting groups.

9. A pharmaceutical composition comprising as an active ingredient the compound or salt of claim 2 in association with a pharmaceutically acceptable carrier.

10. A process for the protection of bone marrow in the course of anti-cancer treatment by chemotherapy, which comprises the i.v. or s.c. administration of an effective amount of a pharmaceutical composition according to claim 9.

* * * * *